US012734186B2

(12) United States Patent
Favre et al.

(10) Patent No.: US 12,734,186 B2
(45) Date of Patent: Sep. 15, 2026

(54) COMPOSITIONS FOR USE IN PROMOTING ACCELERATED BUTYRATE PRODUCTION IN YOUNG CHILDREN

(71) Applicant: SOCIETE DES PRODUITS NESTLE S.A., Vevey (CH)

(72) Inventors: Laurent Favre, Carrouge (CH); Florence Rochat, Montreux (CH); Norbert Sprenger, Savigny (CH)

(73) Assignee: Societe des Produits Nestle S.A., Vevey (CH)

( * ) Notice: Subject to any disclaimer, the term of this patent is extended or adjusted under 35 U.S.C. 154(b) by 541 days.

(21) Appl. No.: 18/257,774

(22) PCT Filed: Dec. 17, 2021

(86) PCT No.: PCT/EP2021/086553

§ 371 (c)(1),
(2) Date: Jun. 15, 2023

(87) PCT Pub. No.: WO2022/129556

PCT Pub. Date: Jun. 23, 2022

(65) Prior Publication Data

US 2024/0316084 A1 Sep. 26, 2024

(30) Foreign Application Priority Data

Dec. 18, 2020 (EP) .................................... 20215290

(51) Int. Cl.

| | |
|---|---|
| ***A61K 31/702*** | (2006.01) |
| ***A23L 33/00*** | (2016.01) |
| ***A61P 1/00*** | (2006.01) |
| ***A61P 3/02*** | (2006.01) |

(52) U.S. Cl.
CPC ............ *A61K 31/702* (2013.01); *A23L 33/40* (2016.08); *A61P 1/00* (2018.01); *A61P 3/02* (2018.01)

(58) Field of Classification Search
None
See application file for complete search history.

(56) References Cited

FOREIGN PATENT DOCUMENTS

| | | | | |
|---|---|---|---|---|
| CN | 108495634 A | | 9/2018 | |
| CN | 108697721 A | | 10/2018 | |
| CN | 110621168 A | | 12/2019 | |
| RU | 2017144045 A | | 6/2019 | |
| WO | 2015071131 | | 5/2015 | |
| WO | WO-2017103019 A1 | * | 6/2017 | .............. A61P 31/04 |
| WO | 2017129650 | | 8/2017 | |
| WO | 2018206434 | | 11/2018 | |
| WO | WO-2018207110 A1 | * | 11/2018 | ................ A61P 1/00 |
| WO | 2020108915 | | 6/2020 | |

OTHER PUBLICATIONS

Russian Office Action for Appl No. 2023115701/10 dated Mar. 31, 2025, 11 pages.
Chinese Office Action from corresponding Chinese Patent Application No. 202180083592.6, dated Mar. 25, 2026. 7 pages.

* cited by examiner

*Primary Examiner* — Dale R Miller
(74) *Attorney, Agent, or Firm* — K&L Gates LLP

(57) ABSTRACT

The present invention relates to composition comprising 2'-FL for use in promoting accelerated butyrate production in the gut thereby preventing and/or treating a health disorder, and/or promoting a health benefit in young children consuming the composition.

9 Claims, 3 Drawing Sheets

COMPOSITIONS FOR USE IN PROMOTING ACCELERATED BUTYRATE PRODUCTION IN YOUNG CHILDREN

CROSS REFERENCE TO RELATED APPLICATIONS

The present application is a National Stage of International Application No. PCT/EP2021/086553, filed on Dec. 17, 2021, which claims priority to European Patent Application No. 20215290.6, filed on Dec. 18, 2020, the entire contents of which are being incorporated herein by reference.

FIELD OF THE INVENTION

The present invention relates to composition comprising 2'-FL for use in promoting accelerated butyrate production in the gut thereby preventing and/or treating a health disorder, and/or promoting a health benefit in young children consuming the composition.

BACKGROUND OF THE INVENTION

The toddlerhood is a period of dramatic changes for children. They discover the world at that time, however by at the same time their body and health face huge challenges discovering new virus and bacteria. During this period toddler need to be better armed acquiring the mature innate and adaptive immune systems. Butyric acid is recognized for its beneficial impact as anti-inflammatory effect and immune boost thereby promoting "protection" (Furusawa 2013). The multiple beneficial effects of butyrate are well documented in mammals and livestock. At the intestinal level, butyrate plays a regulatory role on transepithelial fluid transport, mucosal inflammation and oxidative status, reinforces intestinal barrier function, and influences visceral sensitivity and intestinal motility (Canani, 2011). Oral butyrate supplementation promotes antibacterial activity in intestinal macrophages and restricts dissemination of bacteria beyond the intestinal barrier. Butyric acid also benefits the colonocytes by increasing energy production. Additionally, butyrate has been shown to decrease the incidence of diarrhea (Berni Canani et al., Gastroenterol., 2004; 127(2): 630-634), improve gastrointestinal symptoms in individuals with diarrhea-predominant irritable bowel syndrome (Scarpellini et al., Dig Liver Dis., 2007; 1(1):19-22) and enhance the development of the small intestine in neonatal piglets (Kotunia et al., J Physiol Pharmacol. 2004; 55(2): 59-68). Scientist have shown that products promoting the development of butyrate producers were correlate with increased levels of innate and acquired immunity biomarkers (Berni Canani et al. 2017).
Nevertheless, today there is no real solution easily applicable for toddler.

Today to reinforce protection, probiotic alone or in combination are proposed. Poorly formulated probiotic supplements intended for oral administration often fail to protect bacteria from the challenges of human digestion, meaning bacteria do not reach the small intestine in a viable state and that any feeling of improved health often reduces to a placebo effect. As a result, healthcare professionals are not fully confident with such solution.

Typical prebiotics fiber, like FOS (fructooligosaccharides) and GOS (galactooligosaccharides) have been widely used to stimulate the growth of Bifidobacteria, and in some cases Lactobacilli. However, little is known on their impact in vivo on butyrate producing bacteria. Liu in 2017, have even shown that a significant increase in the relative abundance of *Bifidobacterium* was observed both in FOS and GOS group, while the butyrate-producing bacteria like Phascolarctobacterium in FOS group and Ruminococcus in GOS group were decreased as well as the butyrate production (Liu et al, 2017).

Certain complex HMOs mixtures have also been described to increase butyrate production in the digestive tract of infants (WO 2018/206434).

Finally, butyrate could be directly provided but its taste makes it unsuitable for toddlers and capsules containing butyrate will be not really applicable for toddler on the long term.

It is therefore desirable to identify a nutritional intervention to promote accelerated butyrate production in toddlers thereby preventing and/or treating a health disorder, and/or promoting a health benefit.

There is also a need to deliver such benefits in a manner that is particularly suitable for toddlers, in a manner that does not involve a classical pharmaceutical intervention.

There is a need to deliver such benefits in toddlers in a manner that does not induce side effects and/or in a manner that is easy to deliver, and well accepted by the parents or health care practitioners.

There is also a need to deliver benefits in a manner that does keep the cost of such delivery reasonable and affordable by most.

SUMMARY OF THE INVENTION

Prebiotic effects in the gut can be evaluated, among others, on the basis of health-related bacterial metabolites. These include for instance short-chain fatty acids (SCFA, like acetate, propionate and butyrate), which are generally believed to be positive for colonic health and to support immune protection in the gut and lung for example.

By performing a long term SHIME® experiment, the present inventors have surprisingly found that 2'-FL can promote butyrate production in the distal colon of a toddler at an accelerated pace if compared to what can be observed in an infant who received the same human milk oligosaccharide (results shown in FIG. 1).

By performing a long term SHIME® experiment, the present inventors have also surprisingly found that, similarly to 2'-FL, also other human milk oligosaccharides mixtures comprising 2'-FL [namely for example 2-fucosylactose (2'-FL), difucosyllactose (DFL) and lacto-N-tetraose (LNT) (also identifies as HMO-3 mixture) or 2-fucosylactose (2'-FL), difucosyllactose (DFL) 6'-sialyllactose (6'SL), lacto-N-tetraose (LNT) and 3'-sialyllactose (3'SL) (also identified as HMO-5 mixture) promote butyrate production in the distal colon of a toddler after 3 weeks treatment (results shown in FIG. 2).

The SHIME® is a known continuous model of the human gastrointestinal tract and it is called the Simulator of the Human Intestinal Microbial Ecosystem (SHIME®). This model allows to culture the complex gut microbiota over a longer period under representative conditions for the different intestinal regions. Therefore, the SHIME® does not only allow to obtain detailed information about the fermentation profile of the prebiotic formula, but importantly also about the localization of the intestinal fermentation activity.

The multiple beneficial effects on human health of the short-chain fatty acid butyrate, synthesized from non-absorbed carbohydrate by colonic microbiota, are well documented and also described in the background of the present invention.

Besides the effects of butyrate on carcinogenesis, inflammation and oxidative stress, butyrate has been shown to affect several components of the colonic defense barrier leading to enhanced protection against lumina! antigens.

In addition, recently Schulthess and coll. demonstrate that administration of butyrate induced antimicrobial activity in intestinal macrophages in vivo and increased resistance to enteropathogens (Schulthess et al., 2019, Immunity 50, 432-445).

All the above reported beneficial effects of butyrate production in the gut clearly indicate that increased intestinal butyrate represents a benefit for health and a strategy to bolster host defence without tissue damaging inflammation. They also suggest the importance of rapidly achieving such butyrate production.

It is also to note anyway that fermentation of prebiotic may results in an increase of gas production in the intestine which may induce gut discomfort (bloating, flatulence & cramp).

The inventors also surprisingly demonstrated that even if 2'-FL is well fermented in toddler with accelerated butyrate generation, the production of gas associated to this fermentation process remains relatively low, which represent an additional benefit for such a nutritional intervention in toddlers.

In particular, the present invention relates to compositions comprising 2'-FL, for use in promoting accelerated butyrate production in the gut of a toddler consuming the composition.

The compositions are thereby in particular useful in preventing and/or treating a health disorder, and/or promoting a health benefit in young children.

The health disorder is selected from the list consisting of inflammation, infections, antibiotic associated diarrhea, allergies, metabolic health disorders such as obesity later in life, type 2 diabetes, insulin resistance.

The health benefit is selected from the list consisting of gut maturation, gut brain axis connection, colonic healing especially in case of colitis, anti-cancer effects.

Accordingly, the present invention provides for a nutritional composition comprising 2'-FL for use in preventing and/or treating a health disorder, and/or promoting a health benefit by promoting accelerated butyrate production in the gut of a young child consuming the nutritional composition.

The present invention therefore provides a nutritional composition comprising 2-fucosylactose (2'-FL) for use in a method of preventing and/or treating a health disorder, and/or promoting a health benefit by promoting accelerated butyrate production in the gut of a young child consuming the nutritional composition.

The nutritional composition of the present invention is in particular advantageous for use in a method of preventing and/or treating a health disorder, and/or promoting a health benefit in a young child, by promoting accelerated butyrate production in the gut of a young child consuming the nutritional composition.

The invention also relates to the use of a nutritional composition comprising 2-fucosylactose (2'-FL) in a method of preventing and/or treating a health disorder, and/or promoting a health benefit in a young child by promoting accelerated butyrate production in the gut of a young child consuming the nutritional composition.

Accordingly, the present invention provides for a nutritional composition comprising 2-fucosylactose (2'-FL), difucosyllactose (DFL) and lacto-N-tetraose (LNT) for use in preventing and/or treating a health disorder, and/or promoting a health benefit by promoting accelerated butyrate production in the gut of a young child consuming the nutritional composition.

The present invention therefore provides a nutritional composition comprising 2 fucosylactose (2'-FL), difucosyllactose (DFL) and lacto-N-tetraose (LNT) for use in a method of preventing and/or treating a health disorder, and/or promoting a health benefit by promoting accelerated butyrate production in the gut of a young child consuming the nutritional composition.

The invention also relates to the use of a nutritional composition comprising 2-fucosylactose (2'-FL), difucosyllactose (DFL) and lacto-N-tetraose (LNT) in a method of preventing and/or treating a health disorder, and/or promoting a health benefit in a young child by promoting accelerated butyrate production in the gut of a young child consuming the nutritional composition.

Accordingly, the present invention provides for a nutritional composition comprising 2-fucosylactose (2'-FL), difucosyllactose (DFL) 6'-sialyllactose (6'SL), lacto-N-tetraose (LNT) and 3'-sialyllactose (3'SL) for use in preventing and/or treating a health disorder, and/or promoting a health benefit by promoting accelerated butyrate production in the gut of a young child consuming the nutritional composition.

The present invention therefore provides a nutritional composition comprising 2-fucosylactose (2'-FL), difucosyllactose (DFL) 6'-sialyllactose (6'SL), lacto-N-tetraose (LNT) and 3'-sialyllactose (3'SL) for use in a method of preventing and/or treating a health disorder, and/or promoting a health benefit by promoting accelerated butyrate production in the gut of a young child consuming the nutritional composition.

The invention also relates to the use of a nutritional composition comprising 2 fucosylactose (2'-FL), difucosyllactose (DFL) 6'-sialyllactose (6'SL), lacto-N-tetraose (LNT) and 3'-sialyllactose (3'SL) in a method of preventing and/or treating a health disorder, and/or promoting a health benefit in a young child by promoting accelerated butyrate production in the gut of a young child consuming the nutritional composition.

DETAILED DESCRIPTION OF THE INVENTION

Figure 1:
FIG. 1 shows impact of 2'FL on butyrate production in distal colon for infants and toddlers as reported in Example 1.
Figure 1:
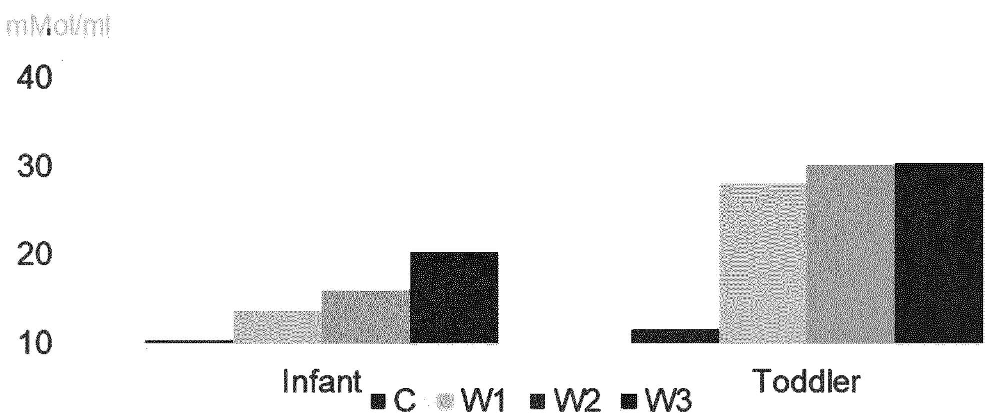

As used herein, the following terms have the following meanings.

The term "infant" means a child under the age of 12 months. The expression "young child" or "toddler" means a child aged between one and less than three years. The expression "child" means a between three and seven years of age.

The expression "nutritional composition" means a composition which nourishes a subject. This nutritional composition is usually to be taken orally or intravenously, and it usually includes a lipid or fat source and a protein source. Non limiting examples of nutritional composition according to the present invention are selected in the group consisting of: infant formula (for example, follow up formula), baby food, infant cereal composition, growing up milk, fortifier and nutritional supplement (for example paediatric supplement).

In a particular embodiment the composition of the present invention is a hypoallergenic nutritional composition. The expression "hypoallergenic nutritional composition" means a nutritional composition which is unlikely to cause allergic reactions.

In a particular embodiment the composition of the present invention is a "synthetic nutritional composition". The expression "synthetic nutritional composition" means a mixture obtained by chemical and/or biological means, which can be chemically identical to the mixture naturally occurring in mammalian milks (i.e. the synthetic composition is not breast milk).

The expression "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter infant formula" and "follow-up formula" or "follow-on formula".

A "follow-up formula" or "follow-on formula" is given from the 6th month onwards. It constitutes the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The expression "growing-up milk" (or GUM) refers to a milk-based drink generally with added vitamins and minerals, that is intended for young children or children.

The term "fortifier" refers to liquid or solid nutritional compositions suitable for fortifying or mixing with human milk, infant formula, growing-up milk or human breast milk fortified with other nutrients. Accordingly, the fortifier of the present invention can be administered after dissolution in human breast milk, in infant formula, in growing-up milk or in human breast milk fortified with other nutrients or otherwise it can be administered as a stand alone composition. When administered as a stand-alone composition, the milk fortifier of the present invention can be also identified as being a "supplement". In one embodiment, the milk fortifier of the present invention is a supplement.

The term "nutritional supplement" refers to a product which is intended to supplement the general diet of a subject.

The term "paediatric supplement" refers to a product which is intended to supplement the general diet of a infant, a young child or a child.

The expression "weaning period" means the period during which the mother's milk is substituted by other food in the diet of an infant or young child.

The expressions "days/weeks/months/years of life" and "days/weeks/months/years of birth" can be used interchangeably.

The expression "later in life" and "in later life" can be used interchangeably. They refer to effects measured in the individual (infant or young child) after the age of some weeks, some months or some years after birth, such as after the age of 6 months after birth, such as after the age of 8 months after birth, such as after the age of 10 months after birth, such as after the age of 1 year after birth, such as after the age of 2 years, preferably after the age of 4 years, more preferably after the age of 5 years, even more preferably after the age of 7 years after birth, or even more, and as a comparison to average observations for subjects of the same age. Preferably it refers to an effect observed after at least 1 year of life, or after at least 2, 5, 7, 10 or 15 years of life. So the expression "later in life" might refer to an observation during infancy, during childhood, during the adolescent period, or during adulthood. Preferably it refers to an observation during childhood, during the adolescent period, or during adulthood.

The expression "health disorder(s)" encompass any health conditions and/or diseases and/or dysfunctions that affect the organism of an individual, including the metabolic ones. Non limiting examples of health disorders according to the present invention are selected in the list consisting of: inflammation, infections, antibiotic associated diarrhea, allergies, metabolic health disorders such as obesity later in life, type 2 diabetes, insulin resistance.

The expression "health benefit(s)" any health benefit that relates to the organism of an individual and/or which may help in preventing any health disorder in such individual. Non limiting examples of health benefits according to the present invention are selected in the list consisting of: gut maturation, gut brain axis connection, colonic healing especially in case of colitis, anti-cancer effects.

"Body mass index" or "BMI" is defined as the value resulting from division of a numerator that is the weight in kilograms by a denominator that is the height in meters, squared. Alternatively, the BMI can be calculated from the weight in pounds as the numerator and the height in inches, squared, as the denominator, with the resultant quotient multiplied by 703. "Overweight" is defined for a human as a BMI between 25 and 30. "Obese" is defined for a human as a BMI greater than 30.

The term "SCFA" means short chain fatty acid(s).

The "mother's milk" should be understood as the breast milk or the colostrum of the mother.

An "oligosaccharide" is a saccharide polymer containing a small number (typically three to ten) of simple sugars (monosaccharides).

The term "HMO" or "HMOs" refers to human milk oligosaccharide(s). These carbohydrates are highly resistant to enzymatic hydrolysis, indicating that they may display essential functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide).

A "fucosylated oligosaccharide" is an oligosaccharide having a fucose residue. It has a neutral nature. Some examples are 2-FL (2'-fucosyllactose), 3-FL (3-fucosyllactose), difucosyllactose, lacto-N-fucopentaose (e.g. lacto-N-fucopentaose I, lacto-N-fucopentaose II, lacto-N-fucopentaose III, lacto-N-fucopentaose V), lacto-N fucohexaose, lacto-N-difucohexaose I, fucosyllacto-N-hexaose, fucosyllacto-N-neohexaose, difucosyllacto-N-hexaose I, difucosyllacto-N-neohexaose II and any combination thereof. Without wishing to be bound by theory it is believed that the fucosyl-epitope of the fucosylated oligosaccharides may act as decoy at the mucosal surface. By a competition effect, it may prevent and/or limit the action of the pathogens responsible of infections (of viral or bacterial origin) or of their secreted components (e.g. toxins), especially by avoiding their binding to natural ligands, and without to be bound by theory, this is believed to therefore reduce the risk of infections/inflammations, and particularly the risk of LRT/ear infections and/or inflammations. In addition, the fucosylated oligosaccharides are thought to boost growth and metabolic activity of specific commensal microbes reducing inflammatory response and creating an environment unfavourable for pathogens thus leading to colonization resistance.

The expressions "fucosylated oligosaccharides comprising a 2'-fucosyl-epitope" and "2-fucosylated oligosaccharides" encompass fucosylated oligosaccharides with a certain homology of form since they contain a 2'-fucosyl-epitope, therefore a certain homology of function can be expected. Without wishing to be bound by theory the 2'-fucosyl-epitope of these fucosylated oligosaccharides is believed to be particularly specific to pathogens (or their secreted components) involved in the LRT and/or ear infections.

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. Suitable examples are LNT (lacto-N-tetraose), para-lacto-N-neohexaose (para-LNnH), LNnT (lacto-N neotetraose) and any combinations thereof. Other examples are lacto-N-hexaose, lacto N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose.

The expression "at least one fucosylated oligosaccharide" and "at least one N acetylated oligosaccharide" means "at least one type of fucosylated oligosaccharide" and "at least one type of N-acetylated oligosaccharide".

A "precursor of HMO" is a key compound that intervenes in the manufacture of HMO, such as sialic acid and/or fucose.

A "sialylated oligosaccharide" is a charged sialic acid containing oligosaccharide, i.e. an oligosaccharide having a sialic acid residue. It has an acidic nature. Some examples are 3-SL (3' sialyllactose) and 6'SL (6' sialyllactose).

The nutritional composition of the present invention can be in solid form (e.g. powder) or in liquid form. The amount of the various ingredients (e.g. the oligosaccharides) can be expressed in g/100 g of composition on a dry weight basis when it is in a solid form, e.g. a powder, or as a concentration in g/L of the composition when it refers to a liquid form (this latter also encompasses liquid composition that may be obtained from a powder after reconstitution in a liquid such as milk, water . . . , e.g. a reconstituted infant formula or a follow-on/follow-up formula or a growing-up milk or an infant cereal product or any other formulation designed for infant nutrition).

The term "prebiotic" means non-digestible carbohydrates that beneficially affect the host by selectively stimulating the growth and/or the activity of healthy bacteria such as bifidobacteria in the colon of humans (Gibson G R, Roberfroid M B. *Dietary modulation of the human colonic microbiota: introducing the concept of prebiotics. J Nutr.* 1995: 125:1401-12).

The term "probiotic" means microbial cell preparations or components of microbial cells with a beneficial effect on the health or well-being of the host. (Salminen S, Ouwehand A. Benno Y. et al. "Probiotics: how should they be defined' Trends Food Sci. Technol. 1999:10 107-10). The microbial cells are generally bacteria or yeasts.

The term "cfu" should be understood as colony-forming unit.

The expression "to promote accelerated butyrate production in the digestive tract of a young child" means that the amount of butyrate (and/or of physiologically acceptable salts or ions thereof), when measured in the individual in the digestive tract i.e. from the mouth to the rectum (and especially in the intestine, such as in the colon or large intestine or in a part thereof such as the caecum), is higher in a young child fed with the nutritional composition according to the present invention (i.e. comprising 2'-FL) in comparison with an infant fed with the same nutritional composition during the same period. In one embodiment, such period is a period of 4 weeks, for example 3 weeks, for example 3 weeks, for example 1 week. The butyrate production in the digestive tract may be measured by techniques known by the skilled person such as by Gas-Liquid Chromatography. In one embodiment, "accelerated butyrate production in the digestive tract of a young child" indicates an increase in the production of such molecular species in distal colon of at least 100% during a period of 1 week, 2 weeks, 3 weeks or 4 weeks.

For example upon treatment with 2'FL butyrate production increased with +192% in the Proximal Colon, and with +156% in the Distal Colon, as compared to increase of production of such molecular species during the three weeks of treatment by action of gut microbiota of an infant consuming the same, respectively +81% and +54%.

All percentages are by weight unless otherwise stated.

In addition, in the context of the invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

Any reference to prior art documents in this specification is not to be considered an admission that such prior art is widely known or forms part of the common general knowledge in the field.

The invention will now be described in further details. It is noted that the various aspects, features, examples and embodiments described in the present application may be compatible and/or combined together.

A first object of the present invention is therefore a nutritional composition comprising 2-fucosylactose (2'-FL), for use in preventing and/or treating a health disorder, and/or promoting a health benefit by promoting accelerated butyrate production in the gut of a young child consuming the nutritional composition.

In one embodiment, the present invention provides for a nutritional composition comprising 2'-FL, DFL and LNT for use in preventing and/or treating a health disorder, and/or promoting a health benefit by promoting accelerated butyrate production in the gut of a young child consuming the nutritional composition.

In another embodiment, the present invention provides for a nutritional composition comprising 2'-FL, 6'-SL, 3'-SL, DFL and LNT for use in preventing and/or treating a health disorder, and/or promoting a health benefit by promoting accelerated butyrate production in the gut of a young child consuming the nutritional composition.

To achieve such benefits, the nutritional composition of the invention is preferably for use in a method of:

- treating and/or preventing a health disorder selected in the list consisting of: inflammation, infections, antibiotic associated diarrhea, allergies, metabolic health disorders such as obesity later in life, type 2 diabetes and insulin resistance; and/or
- promoting a health benefit selected in the list consisting of: gut maturation, gut brain axis connection, colonic healing especially in case of colitis and anti-cancer effects.

In a particularly advantageous embodiment of the present invention, 2'-fucosylactose (2'-FL) is present in the nutritional composition in some particular amounts.

In a preferred embodiment of the invention, 2'FL is present in the nutritional composition in an amount of 0.005-8 g/L of the composition. In some embodiments, 2'FL may be in an amount of 0.01-3 g/L of the composition, such as 0.04-2 g/L or 0.05-1.5 g/L or 0.09-1.2 g/L of the composition. In a particular embodiment, 2'FL is in an amount of 1 g/L of the composition. In another particular embodiment, 2'FL is in an amount of 0.2 g/L of the composition.

2'FL can be present in the nutritional composition in an amount of 0.004-6.8 g/100 g of composition on a dry weight basis, 2'FL may be present in an amount of 0.008-2.4 g/100 g of composition, such as 0.03-1.6 g/100 g or 0.04-1.2 g/100 g or 0.07-1.0 g/100 g of the composition. In a particular embodiment, 2'FL is present in an amount of 0.8 g/100 g of the composition. In another particular embodiment, 2'FL is present in an amount of 0.16 g/100 g of the composition.

In another particular embodiment, 2'FL is in an amount of 5-500 g/L, 10 to 400 g/L, 40 to 300 g/L, 60-200 g/L, 80-180 g/L, 100-150 g/L or 110-130 g/L of the composition. In a particular embodiment, the HMO mix is in an amount of 120 g/L. Such amounts are particularly adequate when the nutritional composition is in the form of a supplement or of a fortifier.

When the supplement or fortifier is in powder form 2'FL is preferably provided in the nutritional composition of the present invention in such an amount of 0.05-5 g, 0.1-4.5 g, 0.15-4 g, 0.2 to 3.5 g, 0.25 to 3, 0.3 to 2.5, 0.35 to 2, 0.4 to 1.5 g, 0.45-1 g, 0.5 to 0.75 g for example 0.6 g per serving.

In one embodiment of the present invention, the nutritional composition comprises human milk oligosaccharides consisting of 2'FL. 2'FL may be synthesised as described for example in "Large-scale synthesis of H-antigen oligosaccharides by expressing *Helicobacter pylori* alpha1,2-fucosyltransferase in metabolically engineered *Escherichia coli* cells" (Drouillard S, Driguez H, Samain E. Angew Chem Int Ed Engl. 2006 Mar. 3; 45(11):1778-80) or be obtained from commercial sources.

In one embodiment of the present invention, 2'FL is combined with DFL and LNT.

In one embodiment of the present invention, 2'FL is combined with DFL, 3-SL, 6-SL and LNT.

In one specific embodiment, the nutritional composition of the present invention comprises an oligosaccharide mixture that consists of 2'FL LNT and DFL.

In another specific embodiment, the nutritional composition of the present invention comprises an oligosaccharide mixture that consists of 2'FL, 6'SL, LNT, DFL and 3'SL.

In one embodiment of the invention, LNT is present in the nutritional composition in an amount of 0.005-3 g/L of the composition. In some embodiments, LNT may be in an amount of 0.01-1.5 g/L of the composition, such as 0.04-1.2 g/L or 0.05-1 g/L or 0.09 0.8 g/L of the composition. In a particular embodiment, LNT is in an amount of 0.5 g/L of the composition. In another particular embodiment, LNT is in an amount of 0.1 g/L of the composition.

LNT can be present in the nutritional composition in an amount of 0.004-2.3 g/100 g of composition on a dry weight basis, LNT may be present in an amount of 0.008-1.2 g/100 g of composition, such as 0.03-0.9 g/100 g or 0.04-0.8 g/100 g or 0.07-0.6 g/100 g of the composition. In a particular embodiment, LNT is present in an amount of 0.38 g/100 g of the composition. In another particular embodiment, LNT is present in an amount of 0.08 g/100 g of the composition.

In a particular embodiment, the LNT is provided in the nutritional of the present invention in such an amount that normal consumption of the nutritional composition or growing-up milk would provide to the infant or young child, respectively the child, consuming it a total daily dose of 0.003-3.9 g, preferably 0.006-2 g or 0.02-1.6 g or 0.03 1.3 g, for example 0.05-1 g per day.

LNT may be synthesised chemically by enzymatic transfer of saccharide units from donor moieties to acceptor moieties using glycosyltransferases as described for example in U.S. Pat. No. 5,288,637 and WO 96/10086.

In one embodiment of the invention, DFL is present in the nutritional composition in an amount of 0.005-1 g/L of the composition. In some embodiments, DFL may be in an amount of 0.008-0.8 g/L of the composition, such as 0.01-0.7 g/L or 0.01-0.6 g/L or 0.01-0.4 g/L of the composition. In a particular embodiment, DFL is in an amount of 0.1 to 0.2 g/L or at 0.15 g/L of the composition. In another particular embodiment, DFL is in an amount of 0.03 g/L or 0.04 g/L of the composition.

DFL can be present in the nutritional composition in an amount of 0.004-0.8 g/100 g powder of the composition. In some embodiments, DFL may be in an amount of 0.006-0.6 g/100 g powder of the composition, such as 0.007-0.54 g/100 g powder or 0.007-0.5 g/100 g powder or 0.007-0.3 g/100 g powder of the composition. In a particular embodiment, DFL is in an amount of 0.08 to 0.16 g/100 g powder or at 0.12 g/100 g powder of the composition. In another particular embodiment, DFL is in an amount of 0.02 g/100 g powder or 0.03 g/100 g powder of the composition.

DFL may be synthesised chemically by enzymatic transfer of saccharide units from donor moieties to acceptor moieties using glycosyltransferases or by a biotechnology process involving production bacteria modified to produce DFL. DFL may also be produced as a by-product during the production of other fucosylated components like 2'FL.

In another embodiment of the invention the nutritional composition may comprise from 0.005-5 g/L of 6'SL, or from 0.008-2.5 g/L, or from 0.01-1 g/L, or from 0.03-0.7 g/L, for example 0.04 or 0.5 g/L.

The nutritional composition according to the invention can contain 0.004-3.8 g of 6'SL per 100 g of composition on a dry weight basis, e.g. 0.006-1.9 g or 0.008-0.8 g or 0.023-0.5 g or 0.031-0.4 of 6'SL per 100 g of composition on a dry weight basis, for example 0.18 g or 0.04 g per 100 g of composition on a dry weight basis.

In a particular embodiment, 6'SL is provided in the nutritional composition of the present invention in such an amount that normal consumption of the nutritional composition or growing-up milk would provide to the infant or young child, respectively the child, consuming it a total daily dose of 0.003 to 6.5 g, preferably 0.005-3.3 g or 0.006-1.3 g or 0.02-0.9 g, for example 0.024-0.7 g per day.

6'SL may be isolated by chromatographic or filtration technology from a natural source such as animal milks. Alternatively, it may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. 6'SL formation can be initiated by acceptor substrates starting from any degree of polymerisation (DP), from DP=1 onwards. Alternatively, 6'SL may be produced by chemical synthesis from lactose and free N'-acetylneuraminic acid (sialic acid).

In another embodiment of the invention the nutritional composition may comprise from 0.005-1.5 g/L of 3'SL, or from 0.01-1.2 g/L, or from 0.03-1 g/L, or from 0.03-0.5 g/L, for example 0.03 or 0.1 g/L.

The nutritional composition according to the invention can contain 0.004-1.2 g of 3'SL per 100 g of composition on a dry weight basis, e.g. 0.007-0.9 g or 0.023-0.77 g or 0.023-0.38 g of 3'SL per 100 g of composition on a dry weight basis, for example 0.023 g or 0.08 g per 100 g of composition on a dry weight basis.

In a particular embodiment, 3'SL is provided in the nutritional composition of the present invention in such an amount that normal consumption of the nutritional composition or growing-up milk would provide to the infant or young child, respectively the child, consuming it a total daily dose of 0.003 to 6.5 g, preferably 0.005-3.3 g or 0.006-1.3 g or 0.02-0.9 g, for example 0.024-0.7 g per day.

3'SL may be isolated by chromatographic or filtration technology from a natural source such as animal milks. Alternatively, it may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. 3'SL formation can be initiated by acceptor substrates starting from any degree of polymerisation (DP), from DP=1 onwards. Alternatively, 3'SL may be produced by chemical synthesis from lactose and free N'-acetylneuraminic acid (sialic acid).

In particular embodiments of the present invention, the nutritional composition, of the present invention can comprise additional human milk oligosaccharides.

Therefore, in a particular embodiment, the nutritional composition further comprises at least one additional fucosylated oligosaccharide. There can be one or several types of fucosylated oligosaccharide(s). The fucosylated oligosaccharide(s) can indeed be selected from the list comprising 3' fucosyllactose, difucosyllactose, lacto-N-fucopentaose (such as lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose (such as fucosyl-lacto-N neohexaose I, fucosyllacto-N-neohexaose II), difucosyllacto-N-hexaose I, difuco-lacto N-neohexaose, difucosyllacto-N-neohexaose I, difucosyllacto-N-neohexaose II, fucosyl-para-Lacto-N-hexaose, tri-fuco-para-Lacto-N-hexaose I and any combination thereof.

In some particular embodiments the fucosylated oligosaccharide comprises a 2' fucosyl-epitope. It can be for example selected from the list comprising 2'-fucosyllactose, difucosyllactose, lacto-N-fucopentaose, lacto-N-fucohexaose, lacto-N-difucohexaose, fucosyllacto-N-hexaose, fucosyllacto-N-neohexaose, difucosyllacto-N-hexaose difuco-lacto-N-neohexaose, difucosyllacto-N-neohexaose, fucosyl-para-Lacto-N-hexaose and any combination thereof.

The fucosylated oligosaccharide(s) may be isolated by chromatography or filtration technology from a natural source such as animal milks. Alternatively, it may be produced by biotechnological means using specific fucosyltransferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

In another particular aspect of the invention, the nutritional composition or the growing-up milk can comprise at least one N-acetylated oligosaccharide in addition to LNT. There can be one or several types of N-acetylated oligosaccharide. In some particular embodiments the N-acetylated oligosaccharide is lacto-N-neotetraose (LNnT), para-lacto-N-neohexaose (para-LNnH) or any combination thereof. In some particular embodiments the N-acetylated oligosaccharide is LNnT. In some particular embodiments where LNnT is present the nutritional composition or the growing-up milk can comprise both LNT and LNnT in a ratio LNT: LNnT between 5:1 and 1:2, or from 2:1 to 1:1, or from 2:1.2 to 2:1.6.

The N-acetylated oligosaccharide(s) may be synthesised chemically by enzymatic transfer of saccharide units from donor moieties to acceptor moieties using glycosyltransferases as described for example in U.S. Pat. No. 5,288,637 and WO 96/10086. Alternatively, LNnT may be prepared by chemical conversion of Keto-hexoses (e.g. fructose) either free or bound to an oligosaccharide (e.g. lactulose) into N acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

In a particularly advantageous embodiment of the present invention, the nutritional composition or the growing-up milk comprises lacto-N-neotetraose (LNnT).

In a particular embodiment, the nutritional composition or the growing-up milk according to the invention can comprise other sialylated oligosaccharide(s) in addition to 6'SL, such as 3'-sialyllactose (3-SL).

The sialylated oligosaccharide(s) may be isolated by chromatographic or filtration technology from a natural source such as animal milks. Alternatively, they may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

The nutritional composition according to the present invention may also comprise other types of oligosaccharide(s) (i.e. other than human milk oligosaccharides mentioned above) and/or at least a fiber(s) and/or at least a precursor(s) thereof. The other oligosaccharide and/or fiber and/or precursor thereof may be selected from the list comprising galacto-oligosaccharides (GOS), fructo-oligosaccharides (FOS), inulin, xylooligosaccharides (XOS), polydextrose and any combination thereof. They may be in an amount between 0 and 10% by weight of composition. In a particular embodiment, the nutritional composition can also contain at least one BMO (bovine milk oligosaccharide).

The nutritional composition according to the present invention may optionally also comprise at least one precursor of oligosaccharide. There can be one or several precursor(s) of oligosaccharide. For example, the precursor of human milk oligosaccharide is sialic acid, fucose or a mixture thereof.

In particular examples the nutritional composition comprises from 0 to 3 g/L of precursor(s) of oligosaccharide, or from 0 to 2 g/L, or from 0 to 1 g/L, or from 0 to 0.7 g/L, or from 0 to 0.5 g/L or from 0 to 0.3 g/L, or from 0 to 0.2 g/L of precursor(s) of oligosaccharide. The composition according to the invention can contain from 0 to 2.1 g of precursor(s) of oligosaccharide per 100 g of composition on a dry weight basis, e.g. from 0 to 1.5 g or from 0 to 0.8 g or from 0 to 0.15 g of precursor(s) of oligosaccharide per 100 g of composition on a dry weight basis.

The nutritional composition of the present invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly Bifidobacteria and/or Lactobacilli.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM 1-2116, *Lactobacillus johnsonii* CNCM 1-1225, *Streptococcus salivarius* DSM 13084 sold by BLIS Technologies Limited of New Zealand under the designation K12, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The nutritional composition or the growing-up milk according to the invention may contain from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments. Probiotic components and metabolites can also be added.

The nutritional composition according to the invention can be for example an infant formula, a starter infant formula, a follow-on or follow-up formula, a growing-up milk, a baby food, an infant cereal composition, a fortifier such as a human milk fortifier, or a supplement.

In some other embodiments the nutritional composition of the present invention is a fortifier. The fortifier can be a breast milk fortifier (e.g. a human milk fortifier) or a formula fortifier such as a follow-on/follow-up formula fortifier.

When the nutritional composition is a supplement, it can be provided in the form of unit doses. In such cases it is particularly useful to define the amount of 2'-FL and optionally other oligosaccharides in terms of daily dose to be administered to the infant or young child, such as described above.

When the nutritional composition is a supplement, it may comprise 2'-FL and no other additional nutrient on top of the excipients necessary to obtain a stable nutritional composition.

The nutritional composition of the present invention can be in solid (e.g. powder), liquid or gelatinous form. In a specific embodiment the nutritional composition is a supplement comprising 2-fucosylactose (2'-FL), wherein the supplement is in powder form and provided in a sachet, preferably a sachet with 0.1 to 20 g per sachet, for example 1 to 10 g of 2-fucosylactose (2'-FL) per sachet, or in the form of a syrup, preferably a syrup with a total solid concentration of 5 to 75 g/100 mL (5 to 75% (w/v)). When the supplement is in powder form, it may comprise a carrier. It is however preferred that the supplement is devoid of a carrier. When the supplement is in the form of a syrup, the HMOs are preferably dissolved or suspended in water acidified with citrate.

The nutritional composition according to the invention generally contains a protein source. The protein can be in an amount of from 1.6 to 3 g per 100 kcal. In some embodiments, especially when the composition is intended for premature infants, the protein amount can be between 2.4 and 4 g/100 kcal or more than 3.6 g/100 kcal. In some other embodiments the protein amount can be below 2.0 g per 100 kcal, e.g. between 1.8 to 2 g/100 kcal, or in an amount below 1.8 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

In some advantageous embodiments the protein source is whey predominant (i.e. more than 50% of proteins are coming from whey proteins, such as 60% or 70%).

The proteins may be intact or hydrolysed or a mixture of intact and hydrolysed proteins. By the term “intact” is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term “hydrolysed” means in the context of the present invention a protein which has been hydrolysed or broken down into its component amino acids. The proteins may be either fully or partially hydrolysed. It may be desirable to supply partially hydrolysed proteins (degree of hydrolysis between 2 and 20%), for example for infants or young children believed to be at risk of developing cow’s milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

In one particular embodiment the proteins of the nutritional composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90.

The protein component can alternatively be replaced by a mixture or synthetic amino acid, for example for preterm or low birth weight infants.

In a particular embodiment the nutritional composition according to the invention is a hypoallergenic composition.

The nutritional composition according to the present invention generally contains a carbohydrate source. This is particularly preferable in the case where the nutritional composition of the invention is a follow up formula or a growing up milk. In this case, any carbohydrate source conventionally found in such products like lactose, sucrose, saccharose, maltodextrin, starch and mixtures thereof may be used although one of the preferred sources of carbohydrates is lactose.

The nutritional composition according to the present invention generally contains a source of lipids. This is particularly relevant if the nutritional composition of the invention is a follow up formula or a growing up milk. In this case, the lipid source may be any lipid or fat which is suitable for use in such products. Some suitable fat sources include palm oil, structured triglyceride oil, high oleic sunflower oil and high oleic safflower oil, medium-chain-triglyceride oil. The essential fatty acids linoleic and a-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

The nutritional composition the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition the invention may contain emulsifiers and stabilisers such as soy, lecithin, citric acid esters of mono- and diglycerides, and the like.

The nutritional composition of the invention may also contain other substances which may have a beneficial effect such as lactoferrin, nucleotides, nucleosides, and the like.

The nutritional composition of the invention may also contain carotenoid(s). In some particular embodiments of the invention, the nutritional composition of the invention does not comprise any carotenoid.

The nutritional composition according to the invention may be prepared in any suitable manner. A composition will now be described by way of example.

For example, a follow up formula may be prepared by blending together the protein source, the carbohydrate source and the fat source in appropriate proportions. If used, the emulsifiers may be included at this point. The vitamins and minerals may be added at this point but they are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture. The fucosylated oligosaccharide(s) and the N-acetylated oligosaccharide(s) may be added at this stage, especially if the final product is to have a liquid form. If the final product is to be a powder, they may likewise be added at this stage if desired.

The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

If the final product is to be a powder, the homogenised mixture is transferred to a suitable drying apparatus such as a spray dryer or freeze dryer and converted to powder. The powder should have a moisture content of less than about 5% by weight. The fucosylated oligosaccharide(s) and the N-acetylated oligosaccharide(s) may also or alternatively be added at this stage by dry-mixing or by blending them in a syrup form of crystals, along with the probiotic strain(s) (if used), and the mixture is spray-dried or freeze-dried.

If a liquid composition is preferred, the homogenised mixture may be sterilised then aseptically filled into suitable containers or may be first filled into the containers and then retorted.

In another embodiment, the composition of the invention may be a supplement. The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

The nutritional composition according to the invention is for use in young children. The young children may be born term or preterm. In a particular embodiment the nutritional composition of the invention is for use in young children that were born preterm, having a low birth weight and/or born small for gestational age (SGA). In a particular embodiment the nutritional composition of the invention is for use in preterm infants, infants having a low birth weight and/or infants born small for gestational age (SGA).

The nutritional composition can be administered (or given or fed) at an age and for a period that depends on the needs.

The nutritional composition can be for example given to the young child starting from the age of 12 months, starting from the age of 16 months, starting from the age of 18 months or starting from the age of 24 months. The composition of the invention can for example be given during one month, during two months, during six months, or during one year.

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement a follow-on/follow-up formula or a growing up milk.

EXAMPLES

The following examples illustrate some specific embodiments of the composition for use according to the present invention. The examples are given solely for the purpose of illustration and are not to be construed as limitations of the present invention.

Example 1

Butyrate and Gas Production—Comparison of Infants and Toddlers in a Model

Protocol

The model of the human gastrointestinal tract used was the SHIME®. The first two reactors are of the fill-and-draw principle to simulate different steps in food uptake and digestion, with peristaltic pumps adding a defined amount of SHIME® feed (140 mL 3×/day) and pancreatic and bile liquid (60 mL 3×/day), respectively to the stomach and small intestine compartment and emptying the respective reactors after specified intervals. The last three compartments simulate the large intestine. The SHIME® experiment for this study consisted of three stages:

- Stabilization period: After inoculation of the colon reactors with a fresh faecal sample, a two-week stabilization period allowed the microbial community to differentiate in the different reactors depending on the local environmental conditions. During this period a basic nutritional matrix was provided to the SHIME to support the optimum diversity of the gut microbiota originally present in the faecal inoculum.
- Control period: During this two-week reference period, the standard SHIME® nutrient matrix was further added to the model for a period of 14 days. Analysis of samples in this period allows to determine the baseline microbial community composition and activity in the different reactors, which will be used as a reference for evaluating the treatment effects.
- Treatment period: During this three-week period, the SHIME® reactor was operated under nominal conditions, but with a diet supplemented with the 2'FL product on top of the normal composition.

The diet supplemented with 2'FL was administered 3 times a day at a concentration of 1%

SCFA Production were Measured Three Times Per Week Throughout the Experiment

Gas production is a measure of fermentative activity by gut microbes. Hence, changes in gas production provide insight in the overall fermentation. Gas production is not monitored in the long-term SHIME® model, given its regular flushing with N2 (to ensure anaerobiosis). Therefore, gas production was evaluated by collecting samples from the proximal colon vessel of the SHIME and treating them with lactose or 2'-FL in a penicillin tube. It was then incubated for 24 h and 48 h. The gas formation was assessed in those tubes.

Results

Figure 5:
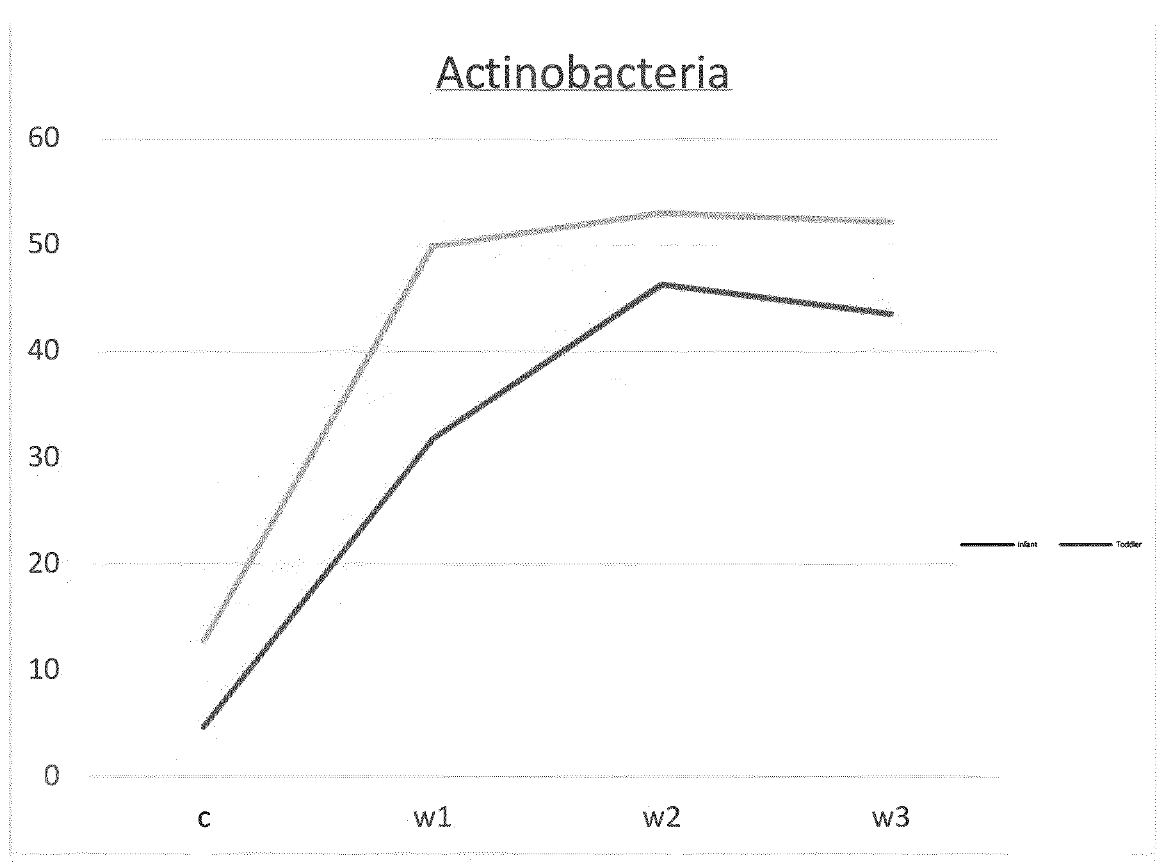
FIG. 5 shows the immediate bifidogenic effect of 2'-FL for toddlers vs infants (increase in Actinobacteria and particularly in Bifidobacteria).

The treatment with 2'FL resulted in following effects in the colon:

An immediate increase of the butyrate concentration in the colon, was observed in the experiment with toddler samples. Then the butyrate concentrations were relatively stable throughout the treatment period (FIG. 1 and Table 1). In the same experiment performed with infant fecal samples the increase in butyrate was more gradual over the weeks of treatment. During these experiments component of the microbiota were measured and it was observed for Actinobacteria phylum mainly composed of Bifidobacteria an immediate effect of 2FL for toddlers (FIG. 5 and Table 2).

TABLE 1

Impact of 2'FL on butyrate concentration in colon model (mM/m1)

| | Control | Treatment | | |
|---|---|---|---|---|
| | Period | week 1 | week 2 | week 3 |
| Infant | 10.45 | 13.75 | 15.85 | 20.3 |
| Toddler | 10.45 | 28.1 | 30.2 | 30.3 |

TABLE 2

Impact of 2'FL on the Actinobacteria population in toddler and infant (colon model) (Abundance in %)

| | Control | Treatment | | |
|---|---|---|---|---|
| | Period | week 1 | week 2 | week 3 |
| Infant | 4.7 | 31.8 | 46.3 | 43.5 |
| Toddler | 12.8 | 49.9 | 53 | 52.2 |

Figure 3:
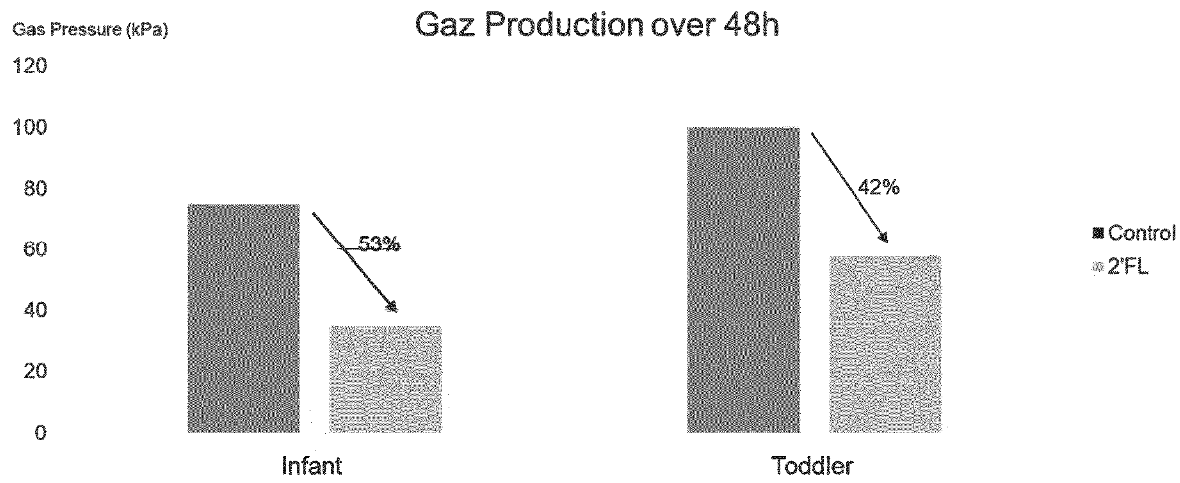
FIG. 3 shows the gas production resulting of 2'-FL fermentation for infants and toddlers as reported in Example 1.

Gas production mainly occurred between 6-24 h. Within this timeframe, gas production was highest for Lactose (control) and lowest for 2'FL. Gas production during the final 24 h was considerably lower as compared to the 0-24 h time frame. Globally less gas production was observed with 2'FL in both toddler and infant over 48 hours (as shown in FIG. 3 and Table 3) as compared to Lactose. Surprisingly, despite the accelerated butyrate production in toddlers, there was no corresponding increase in gas production.

TABLE 3

Impact of 2'FL on the gas production at 48 h (gaz pressure kPA)

| | Control | 2'-FL |
|---|---|---|
| Infant | 4.7 | 31.8 |
| Toddler | 12.8 | 49.9 |

Example 2

Model of Butyrate Production—Comparison of Different HMOs Blends Protocol

The model of the human gastrointestinal tract used was the SHIM ED. The first two reactors are of the fill-and-draw principle to simulate different steps in food uptake and digestion, with peristaltic pumps adding a defined amount of SHIME feed (140 mL 3×/day) and pancreatic and bile liquid (60 mL 3×/day), respectively to the stomach and small intestine compartment and emptying the respective reactors after specified intervals. The last three compartments simulate the large intestine. The SHIME® experiment for this study consisted of three stages:

- Stabilization period: After inoculation of the colon reactors with a fresh faecal sample, a two-week stabilization period allowed the microbial community to differentiate in the different reactors depending on the local environmental conditions. During this period a basic nutritional matrix was provided to the SHIME to support the optimum diversity of the gut microbiota originally present in the faecal inoculum.
- Control period: During this two-week reference period, the standard SHIME nutrient matrix was further added to the model for a period of 14 days. Analysis of samples in this period allows to determine the baseline microbial community composition and activity in the different reactors, which will be used as a reference for evaluating the treatment effects.
- Treatment period: During this three-week period, the SHIME reactor was operated under nominal conditions, but with a diet supplemented with the 2'FL product on top of the normal composition or with the mixtures HMO-3 or HMO-5.

The diet supplemented with HMOs administered 3 times a day at a concentration of 1%. In this experiment, also branched SCFA (b-SCFA=sum of isobutyrate, isovalerate and isocaproate) were measured which result from protein degradation and reflect proteolytic activity of the gut microbiota. A significant alterations in those metabolites was shown in fecal extracts from patients with colon cancer compared to controls Ref: Le Gall 2018 (Oncotarget, 2018, Vol. 9, (No. 70), pp: 33278-33289)

Results

Figure 2:
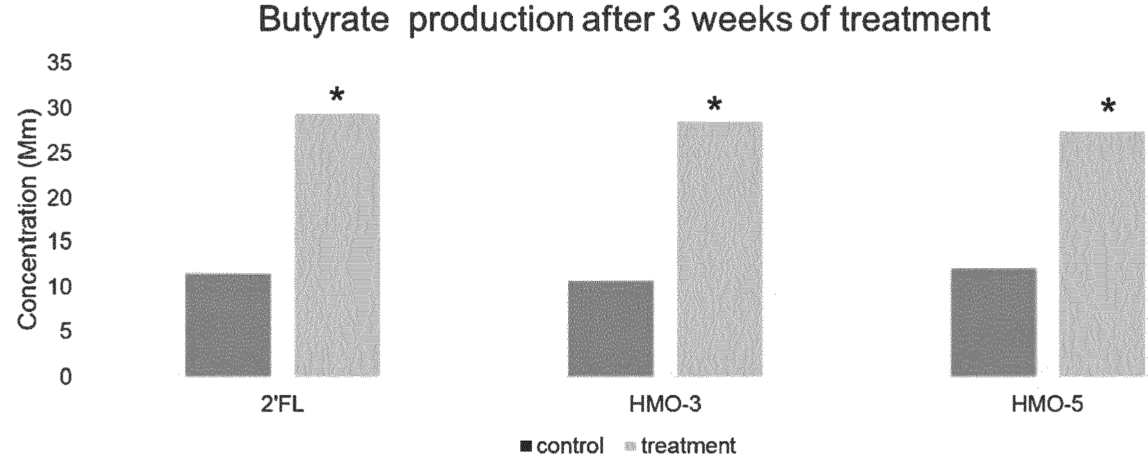
FIG. 2 shows the effect of three different human milk oligosaccharide compositions 2' FL, a Mix of 2-fucosylactose (2'-FL), difucosyllactose (DFL) and lacto-N-tetraose (LNT) (also indicated as HMO-3), and a Mix of comprising 2-fucosylactose (2'-FL), difucosyllactose (DFL) 6'-sialyllactose (6'SL), lacto-N-tetraose (LNT) and 3'-sialyllactose (3'SL) (also indicated as (HMO-5) on butyrate production in distal colon. Average weekly butyrate production during control period (C) and treatment (TR) weeks is shown. An asterisk indicates statistically significant differences relative to the preceding period.

The treatment with 2'FL resulted (FIG. 2 and Table 4) an immediate increase of butyrate production in the colon.

The treatment with HMO-3 resulted in (FIG. 2 and Table 4) an immediate increase of butyrate production in the colon. Butyrate production were stable throughout the whole treatment period.

The treatment with HMO-5 resulted (FIG. 2 and Table 4): an immediate increase of butyrate production in the colon. Butyrate production were stable throughout the whole treatment period.

TABLE 4

Impacts of HMOs mixes on butyrate production in toddler (mM).

| | 2'-FL | HMO 3 | HMO 5 |
|---|---|---|---|
| Control | 11.5 | 10.7 | 12.1 |
| week 3 | 29.5 | 28.5 | 27.5 |

Figure 4:
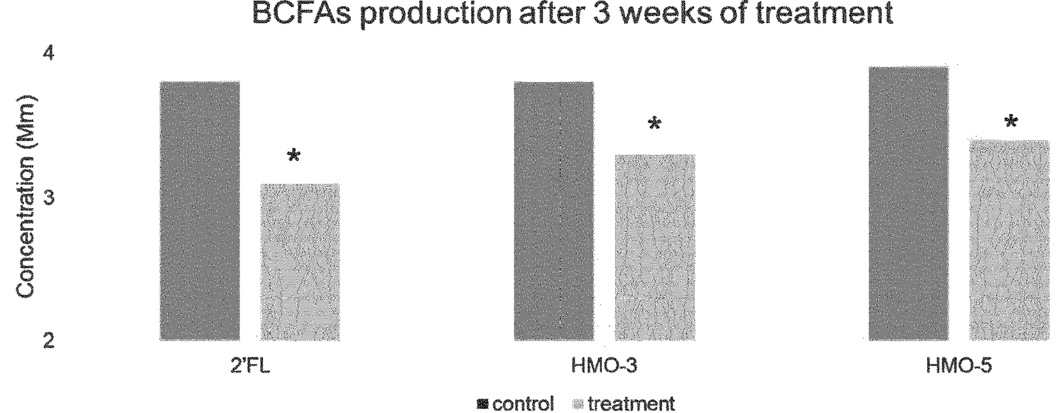
FIG. 4 shows the effect of three different human milk oligosaccharide compositions 2'-FL, a Mix of 2-fucosylactose (2'-FL), difucosyllactose (DEL) and lacto-N-tetraose (LNT) (also indicated as HMO-3), and a Mix of comprising 2-fucosylactose (2'-FL), difucosyllactose (DFL) 6'-sialyllactose (6'SL), lacto-N-tetraose (LNT) and 3'-sialyllactose (3'SL) (also indicated as (HMO-5) on branched fatty acids (BCFA) production in distal colon. Average weekly BCFA production during control period (C) and treatment (TR) weeks is shown. An asterisk indicates statistically significant differences relative to the preceding period.

BCFA levels decreased for all treatments. Differences were statistically significant in all cases (FIG. 4).

TABLE 5

| Impacts of HMOs mixes on BCFA production in toddler (mM). | | | |
|---|---|---|---|
| | 2'-FL | HMO 3 | HMO 5 |
| Control | 3.8 | 3.8 | 3.9 |
| week 3 | 3.1 | 3.3 | 3.4 |

Example 3

An example of the composition of a nutritional composition (e.g. for example a follow up formula) according to the present invention is given in the below table 1. This composition is given by way of illustration only.

TABLE 1

| Nutrients | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| 2'-FL | 0.15 | 1.0 |

The invention claimed is:

1. A method to prevent and/or treat a health disorder, and/or to promote a health benefit in a young child aged between one and less than three years compared to an infant under 12 months of age, wherein the health disorder is selected from the group consisting of inflammation, infections, allergies, metabolic health disorders and wherein the health benefit is selected from the group consisting of gut maturation, gut brain axis connection, and colonic healing comprising administering a nutritional composition comprising 2-fucosylactose (2'-FL), that promotes accelerated butyrate production in the gut of the young child consuming the nutritional composition, wherein the butyrate production is increased in the distal colon by at least 100% during a period of 1 week, 2 weeks, 3 weeks or 4 weeks.

2. The method according to claim 1, wherein the 2'FL is present in an amount of 0.005 to 8 g/L of the nutritional composition on a dry weight basis.

3. The method according to claim 1, wherein the nutritional composition comprises human milk oligosaccharides consisting of 2'-FL.

4. The method according to claim 1, wherein the nutritional composition further comprises DFL and LNT.

5. The method according to claim 1, wherein the nutritional composition further comprises 6'-SL, 3'-SL, DFL and LNT.

6. The method according to claim 1, wherein the nutritional composition is in a form selected from the group consisting of a follow-on or follow-up infant formula, a growing-up milk, a baby food, an infant cereal composition, a fortifier and a supplement.

7. The method according to claim 1, wherein the 2'FL is present in an amount of 0.04 to 2 g/L of the nutritional composition on a dry weight basis.

8. The method according to claim 1, wherein the nutritional composition is administered to the young child starting from an age of 12 months, 16 months, 18 months, or 24 months.

9. The method according to claim 1, wherein the nutritional composition is administered to the young child for one month, two months, six months or one year.

* * * * *